United States Patent [19]
Uekama et al.

[11] Patent Number: 5,904,929
[45] Date of Patent: May 18, 1999

[54] ACYLATED CYCLODEXTRIN-CONTAINING PHARMACEUTICAL COMPOSITION

[75] Inventors: Kaneto Uekama; Fumitoshi Hirayama, both of Kumamoto; Akira Kondo, Shizuoka-ken; Masaaki Ohta, Shizuoka-ken; Yasuhiro Okamoto, Shizuoka-ken; Haruo Kunihiro, Tokyo, all of Japan

[73] Assignee: Janssen Pharmaceutica, N.V., Beerse, Belgium

[21] Appl. No.: 08/886,934

[22] Filed: Jul. 2, 1997

[51] Int. Cl.⁶ ............................ A61K 9/70; A61K 31/715
[52] U.S. Cl. ............................ 424/443; 514/58; 514/181; 514/213; 514/947
[58] Field of Search ..................... 514/213, 58, 947, 514/181; 424/443

[56] References Cited

U.S. PATENT DOCUMENTS 5,633,368  5/1997  Hirsenkorn ........................ 536/103

OTHER PUBLICATIONS

Chemical Abstracts 118:197895e (Kawahara et al), 1993.
Chemical Abstract 124:59731w (Hirenkorn) (From EP 678, 525; Oct. 1995), 1996.

Matsubara, K., et al., Controlled Release of the LHRH Agonist Buserelin Acetate from Injectable Suspensions Containing Triacetylated Cyclodextrins in an Oil Vehicle, J. of Controlled Release, 31 (1994) pp. 173–180.

Uekama, K., et al., Peracylated B–Cyclodextrins as Novel Sustained–Release Carriers for a Water–Soluble Drug, Molsidomine, J. of Phar. Pharmacol. (1994) 46, pp. 714–717.

Hirayama F., et al., Enhanced Bioavailability and Reduced Metabolism of Salbutamol by Perbutanoyl–B–Cyclodextrin After Oral Administration in Dogs, Pharmaceutical Sciences (1995), vol. 1, pp. 517–520.

Hirayama, F., et al., Characterization of Peracylated B–Cyclodextrins with Different Chain Lengths as a Novel Sustained Release Carrier for Water–Soluble Drugs, Chem. Pharm. Bulletin 43 (1995) pp. 130–136.

*Primary Examiner*—Leonard Schenkman
*Attorney, Agent, or Firm*—Mary A. Appollina

[57] ABSTRACT

A pharmaceutical composition for trans-mucosal or transdermal administration wherein a per-$C_{2-18}$ acylated cyclodextrin is used as a drug reservoir or carrier. The composition can be used safely and exhibits excellent drug release behavior.

2 Claims, 3 Drawing Sheets

ACYLATED CYCLODEXTRIN-CONTAINING PHARMACEUTICAL COMPOSITION

CROSS-REFERENCE TO RELATED APPLICATION

This application claims priority from Japanese application JP 356,054/96, filed Dec. 25, 1996.

BACKGROUND OF THE INVENTION

1. Field of the Invention

This invention relates to the use of peracylated cyclodextrin in a pharmaceutical composition, and more specifically, relates to a pharmaceutical composition wherein a per-$C_{2-18}$ acylated cyclodextrin is used as a drug carrier, and further to a process for preparing such a composition having a specified form.

2. Description of Prior Arts

Cyclodextrin (hereinafter, referred to as CyD) is an oligosaccharide wherein glucose residues are cyclically bound through $\alpha$-1,4 bond. Those which are each composed of 6, 7 or 8 glucose residues and each of which is called $\alpha$, $\beta$ or $\gamma$-CyD respectively have been put to practical use. These CyDs have a high clathrating ability on certain chemical substances, and are utilized, in the field of pharmaceuticals, food and cosmetics, for various uses such as stabilization, retention of volatile substances and solubilization of substances which are sparingly soluble or insoluble in water.

Further, for the purpose of utilizing such physicochemical characteristics and clathrating ability of CyD as a multifunctional drug carrier, etc., various CyD derivatives are provided. For example, partially acylated cyclodextrin for solubilizers, preparation aids, stabilizing agents, degreasing agents, solvent-substitutes, and further, coating materials, fixing aids, phase transfer catalysts and masking agents on the sense of taste and the sense of smell are described in Japanese Laid-Open (Kokai) Patent Publication No. 35 300501/1995.

Furthermore, there can be taken, as noteworthy compounds, heptakis (2,3,6-tri-0-acetyl)-$\beta$-cyclodextrin and octakis (2,3,6-tri-0-acetyl)-$\gamma$-cyclodextrin for use in combination with an water-soluble drug described in K. Uekawa et al., J. Controlled Release, 31 (1994), 173–180, and peracylated $\beta$-cyclodextrins described in J. Pharm. Pharmacol. 1994, 46: 714–717; Chem. Pharm. Bull. 43 (1995), 130–136 and Pharmaceutical Science 1995, 1: 517–520. As for these peracylated $\beta$-cyclodextrins, there have been disclosed those having acyl groups having 2 to 12 carbon atoms, among which some that have a certain chain length can be used in combination with a water-soluble drug such as morsidomine or salbutamol to form a preparation which is interesting in that, when orally administered to experimental animals, it allows the release rate of the drug to be controlled. In the above J. Pharm. Pharmacol. 1994, 46: 714–717, it is shown that particularly, perbutanoyl ($C_4$)-$\beta$-CyD remarkably retards the drug release rate, compared with other aclated $\beta$-CyDs. It has been suggested that this action is caused by the appropriate adhesion to mucosa and hydrophobicity of perbutanoyl-$\beta$-CyD.

On the other hand, attention has been drawn in recent years to the development of pharmaceuticals for the trans-mucosal or transdermal administration of drugs which have systemic or topical actions toward various diseases, with a view to decreasing compliance of patients. However, since it is difficult to control the release of drugs from pharmaceuticals, it has been necessary to use various additives or, in the case of solid drugs, to employ a solvent to dissolve the solid drugs with. Further, there is a case where it is necessary to select additives to be compounded for the purpose of controlling the release of drug or promoting its absorption or solvents for dissolving the drug. These materials are, however, generally irritative to skin or cutis, thus causing problems that long-term use is difficult. Particularly, many of absorption enhancers for drugs have generally a high solubility in lipid, and it is said that almost all of the above absorption enhancers interact with the adhesives in transdermal absorption compositions, with the result that adhesion or adhesive force between the pharmaceuticals and the cutis is adversely influenced (Development of Pharmaceuticals, 12, page 374, Chapter 3 Pharmaceutical Materials Expectable in New Functions, published by Hirokawa Shoten in 1988).

In order to overcome these problems, it has been proposed to place a drug reservoir and an absorption enhancer reservoir separately, or there has been proposed a peripheral-type pharmaceuticals for transdermal absorption wherein the adhesives are placed only at the periphery, as in tranzone, and, thus, certain results have been attained.

However, there are still needs for a composition for trans-mucosal or transdermal administration which is easy to prepare, excellent in drug releasability from the pharmaceutical composition and excellent in absorptivity in a living body of the released drug. Thus, the object of the invention lies in providing a pharmaceutical composition satisfying the above needs.

SUMMARY OF THE INVENTION

In order to solve the above problems, the present inventors have studied the trans-mucosal and transdermal administration of various compositions. As a result, they have found that certain peracylated cyclodextrins are excellent not only in the adhesion to mucosa, but in the releasability of the drugs from compositions prepared therefrom, and moreover, heighten the absorptivity of the released drugs into living bodies.

Thus, according to the invention, there is provided a pharmaceutical composition for the trans-mucosal or transdermal administration comprising a per-$C_{2-18}$ acylated cyclodextrin as a solubilizing agent, adsorbent or clathrating agent, and a drug.

Another object of the present invention is to provide a pharmaceutical composition for the trans-mucosal or transdermal administration comprising the per-$C_{2-18}$ acylated cyclodextrin and the drug, said composition being in the form of a sheet or film.

Yet another object of the present invention is to provide a method for the trans-mucosal or transdermal administration of a drug which comprises applying said composition to the mucosa or cutis of an individual who needs to be treated with the drug.

Still another object of the present invention is to provide a process for preparing a sheet-like or filmy pharmaceutical composition using the acylated cyclodextrin.

Although not bound by the theory, it is surmised that, according to the composition of the invention, the acyl groups densely standing in a row on the CyD molecule heighten the adhesion to mucosa and cutis, and further that, if the composition is molded into a sheet-like or filmy form, the acyl groups form an environment rich in air tightness, prevent transpiration, etc. of water from the applied surface, and thereby heighten the cutis-permeability of drugs. Further, the per-$C_{2-18}$ acylated CyD used in the invention is very low in irritativeness on mucosa and cutis. Besides, the per-$C_{2-18}$ acylated CyD used in the invention takes a solid, liquid or wax-like form, and it is guessed that, when combined with a drug, said compound will act as a solubilizing agent (or solvent), adsorbent or clathrating agent.

DETAILED DESCRIPTION OF THE INVENTION

Figure 1:
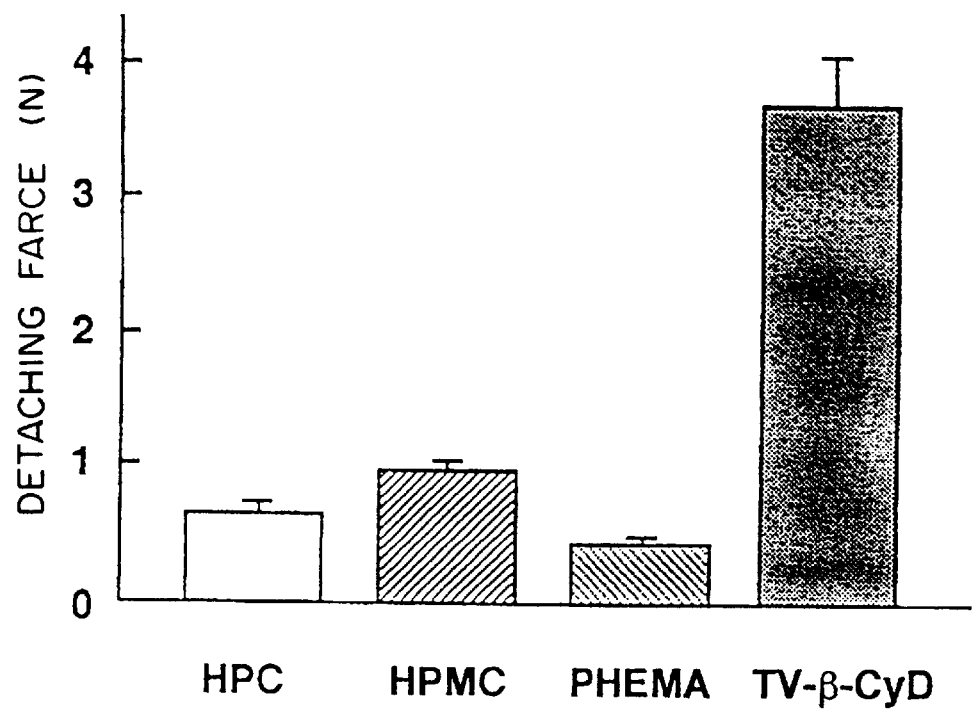
FIG. 1 is a graph which shows comparison on detaching force between trivaleryl-β-cyclodextrin and the various hydrophilic macromolecules, using a probe tack tester.

The term "per-$C_{2-18}$ acylated" in the invention means that all the hydroxyl groups in the cyclodextrin molecule are acylated. So long as the object of the invention is achieved, the term also includes the case where 90% or more in average of all the hydroxyl groups in the cyclodextrin molecule (e.g., 21 in β-CyD) are acylated. The acylation rate is preferably 95% or more, but 100% (i.e., all the hydroxyl groups in CyD are completely acylated) is most desirable.

Further, the cyclodextrin in the invention includes not only the above-mentioned α-CyD, β-CyD and γ-CyD, but so-called branched CyDs wherein one or plural glucose residues are added thereto, but β-CyD is particularly preferred. Thus, although hereinafter, the invention is described citing β-CyD for making the description concise, it should be understood that other CyDs can be treated in the same manner and have the similar actions. When the above CyD wherein 100% of the hydroxyl groups are acylated is more specifically expressed, it corresponds to heptakis (2,3,6-tri-0acyl)-β-cyclodextrin.

Specific examples of the acyl groups which are referred to in the $C_{2-18}$ acylation include acetyl, propanoyl, butanoyl, pentanoyl (or valeryl), hexanoyl (or caproyl), heptanoyl (or enanthyl), octanoyl (or capryloyl), dodecanoyl (or lauroyl), tetradecanoyl (or myristoyl), octadecanoyl (or stearoyl) groups, etc., and acyl groups derived from branched chain fatty acids corresponding thereto, but acyl groups derived from straight-chain fatty acids are preferably used. These acyl groups can be the same or different, but convenience on preparation being taken into account, it is preferred that all the acy groups are the same.

Further, if the acylated CyD used in the invention has the same acyl group, ones having 4 to 8 carbon atoms are preferred, and ones having 4 to 6 carbon atoms are particularly preferred. For example, per-$C_5$ acylated β-CyD has, as such, film formability, and per-$C_4$ acylated β-CyD or per-C6 acylated β-CyD can also be molded into film, if needed by adding a film forming-high molecular compound or the like, and the film can conveniently be used as a pharmaceutical composition for trans-mucosal or transdermal administration according to the invention.

Thus, according to the invention, the acylated CyD can readily be molded, as the form of the composition, into a filmy form and a sheet-like form. Although its details are made clear later, there is a case wherein, as to the composition molded into the form of a sheet or film, the release patterns of the drug somewhat differ between the side of the casting surface and the side of the opposite surface, and it is also possible to choose the surface to be applied to the mucosa or cutis, in accordance with the purpose of the drug used.

As to the composition of the invention molded into a filmy or sheet-like form as stated above, its affinity to the surface to be applied can be adjusted by treating the surface by a suitable method to cause partial deacylation. As this treating method, there can be mentioned alkali treatment or treatment with a suitable deacylating enzyme. The thus obtained partially deacylated composition of the invention is preferred especially in the point that if it is administered to a mucosa under an aqueous environment, for example the oral mucosa, the retentivity of the composition on the mucosa is improved. Thus, a composition wherein partial deacylation is made by surface treatment of the above composition of the invention is also provided according to the invention.

As drugs to be incorporated in the composition according to the invention, any drugs including water-soluble and water-sparingly soluble ones can be used so long as they are in line with the object of the invention, but from the standpoint that they are trans-mucosally or transdermally administered, there can, for example, be mentioned nonsteroidal antirheumatic agents, steroids, cardiac glycosides, benzodiazepine derivatives, benzimidazole derivatives, piperidine derivatives, piperazine derivatives, imidazole derivatives and triazole derivatives. Although not limited thereto, as benzimidazole derivatives, there can be mentioned thiabendazole, fuberidazole, oxibendazole, parbendazole, cambendazole, mebendazole, fenbendazole, flubendazole, albendazole, oxfendazole, nocodazole and astemizole. Further, as suitable piperidine derivatives, there can be mentioned bruspirilen, bimotide, penfluridol, loperamide, ketanserin, levocabastine, cisapride, altanserin and ritanserin. Further, as suitable piperazine derivatives, there can be mentioned lidoflazine, flunarzine, mianserin, oxatomide, miofurazine and cinnarizine. Further, as suitable imidazole derivatives, there can be mentioned metronidazole, ornidazole, ipronidazole, tindazole, isoconazole, nimorazole, primamide, methiamide, metomidate, enilconazole, etomidate, econazole, clotrimazole, garnidazole, cimetidine, docodazole, sulconazole, parconazole, orconazole, butoconazole, triadiminol, Tioconazole, parconazole, fluotrimazole, ketoconazole, oxyconazole, rombazole, bifonazole, oxcimetidine, fenticonazole and tabrazole. Further, as suitable triazole derivatives, there can be mentioned birazole, itraconazole and terconazole. Further, a nitrous acid derivatives such as, isosorbide dinitrate or nitroglycerin can also preferably be incorporated in the composition of the invention.

In addition to the above drugs, this invention covers also the following drugs, which are classified according to their efficacy:

analgesic and anti-inflammatory drugs such as acetylsalicylic acid, sodium diclofenac, ibuprofen, indomethacin, ketoprofen, sodium meclofenamate, mefenamic acid, sodium naproxen, paracetamol, piroxicam and sodium tolmetin;

anti-arrhythmic drugs such as procainamide HCl, quinidine sulphate and verapamil HCl;

antibacterial agents such as amoxicillin, ampicillin, benzathine penicillin, benzylpenicillin, cefaclor, cefadroxil, cephalexin, chloramphenicol, ciprofloxacin, clavulanic acid, clindamycin HCl, doxycycline HCl, erythromycin, sodium flucloxacillin, kanamycin sulphate, lincomycin HCl, minocycline HCl, sodium nafcillin, nalidixic acid, neomycin, norfloxacin, ofloxacin, oxacillin and potassium phenoxymethyl-penicillin;

anti-coagulants such as warfarin;

antidepressants such as amitriptyline HCl, amoxapine, butriptyline HCl, clomipramine HCl, desipramine HCl, dothiepin HCl, doxepin HCl, fluoxetine, gepirone, imipramine, lithium carbonate, mianserin HCl, milnacipran, nortriptyline HCl and paroxetine HCl;

anti-diabetic drugs such as glibenclamide;

antifungal agents such as amphotericin, clotrimazole, econazole, fluconazole, flucytosine, griseofulvin, itraconazole, ketoconazole, miconazole nitrate and nystatin;

antihistamines such as astemizole, cinnarizine, cyproheptadine HCl, flunarizine, oxatomide, promethazine and terfenadine;

anti-hypertensive drugs such as captopril, enalapril, ketanserin, lisinopril, minoxidil, prazosin HCl, ramipril and reserpine;

anti-muscarinic agents such as atropine sulphate and hyoscine;

antivirals such as acyclovir, AZT, ddC, ddI, ganciclovir, loviride, tivirapine, 3TC, delavirdine, indinavir, nelfinavir, ritonavir and saquinavir;

sedating agents such as alprazolam, buspirone HCl, chlordiazepoxide HCl, chlorpromazine, clozapine, diazepam, flupenthixol HCl, fluphenazine, flurazepam, lorazepam, mazapertine, olanzapine, oxazepam, pimozide, pipamperone, piracetam, promazine, risperidone, selfotel, seroquel, sulpiride, temazepam, thiothixene, triazolam, trifluperidol and ziprasidone;

anti-stroke agents such as lubeluzole, lubeluzole oxide, riluzole, aptiganel, eliprodil and remacemide;

anti-migraine drugs such as alniditan and sumatriptan;

beta-adrenoreptor blocking agents such as atenolol, carvedilol, metoprolol, nebivolol and propranolol;

cardiac inotropic agents such as digitoxin, digoxin and milrinone;

corticosteroids such as beclomethansone dipropionate, betamethasone, dexamethasone, hydrocortisone, methylprednisolone, prednisolone, prednisone and triamcinolone;

disinfectants such as chlorhexidine;

diuretics such as acetazolamide, frusemide, hydrochlorothiazide and isosorbide;

anti-Parkinsonian drugs such as bromocryptine mesylate, levodopa and selegiline HCl;

enzymes or essential oils such as anethole, anise oil, caraway, cardamom, cassia oil, cinelole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol and thyme;

gastro-intestinal agents such as cimetidine, cisapride, clebopride, diphenoxylate HCl, domperidone, famotidine, lansoprazole, loperamide HCl, loperamide oxide, mesalazine, metoclopramide HCl, mosapride, olsalazine, omeprazole, ranitidine, rabeprazole, ridogrel and sulphasalazine;

haemostatics such as aminocaproic acid;

lipid regulating agents such as lovastatin, pravastatin, probucol and simvastatin;

local anaesthetics such as benzocaine and lignocaine;

opioid analgesics such as buprenorphine HCl, codeine, dextromoramide and dihydrocodeine;

parasympathomimetics such as galanthamine, neostigmine, physostymine, tacrine, donepezil, ENA 713 (exelon) and xanomeline; and vasodilators such as amlodipine, buflomedil, amyl nitrite, diltiazem, dipyridamole, glyceryl trinitrate, isosorbide dinitrate, lidoflazine, molsidomine, nicardipine, nifedipine, oxpentifylline and pentaerythritol tetranitrate.

In the composition according to the invention, the compounding ratio between the peracylated CyD and the drug can be any ratio so long as it meets the object, but from the standpoint to control the releasability of the drug from the composition, it is possible to choose, as the ratio of the peracylated CyD to the drug, 1:4 to 4:1, preferably 1:2 to 2:1, as molar ratio.

Further, the composition of the invention can, if necessary, contain other pharmaceutically acceptable auxiliaries or additives in such a range that the object of the invention is not adversely influenced. Examples of such auxiliaries or additives include absorption enhancers or skin permeability enhancers for drugs, physical property improvers, stabilizers, etc.

Examples of absorption enhancers include 1-dodecylhexahydro-2H-azepin-2-one, fatty acids such as oleic acid, pyrrolidone derivatives such as N-methylpyrrolidone, thioglycolates such as potassium thioglycolate or calcium thioglycolate, fatty acid alcohol esters such as diisopropyl adipate, enamines, salicylic acid derivatives, sodium caprate, menthol, and the like. The absorption propoters may be added to the composition in about up to 0.5%, preferably in about 1% to about 10%, by weight per total weight of the composition. Examples of physical property improvers include surfactants such as polyoxyethylene fatty acid esters, polyoxyethylene polyoxypropylene block copolymers and fatty acid glycerol esters, thickeners such as xanthane gum, carboxyvinyl polymers, sodium carboxymethylcellulose, polyvinyl pyrrolidone, methylcellulose, hydroxypropy cellulose and propylcellulose, and colorants such as food dyes and iron oxides. Examples of stabilizers include antioxidants such as ascorbic acid, ascorbic palmitate, thioglycerol, dl-α-tocophelol, butylhydroxytoluene, butylhydroxyanisole and propyl gallate, and preservatives such as benzalkonium chloride, sorbic acid and paraoxybenzoic acid esters such as methyl paraben, ethylparaben and benzylalcohol.

The composition according to the invention can be produced by a formulation method known per se, but can preferably be produced as follows.

Peracylated β-CyD and a drug are dissolved in an organic solvent incompatible with water, this solution is added dropwise onto a water surface and developed, and the solvent is volatilized to give a filmy composition having adhesion. In this connection, as conditions for removing the organic solvent, there can be chosen a condition fit for the drug such as ordinary pressure and ordinary temperature, heating under ordinary pressure or heating under reduced pressure or the like. Further, it is possible to obtain a filmy composition having adhesion by dissolving peracylated β-CyD and a drug in an organic solvent, adding dropwise the solution onto aluminum foil, polyethylene terephthalate film, polystyrene film or the like, developing it, and volatilizing the solvent in the same manner as mentioned above. If such a process is used and pervaleryl ($C_5$)-β-CyD is used as the peracylated β-CyD, a transparent filmy composition can be obtained without using other additives.

It is not disclosed in prior art literatures that such a filmy composition can be obtained, and herein, there is provided, as another embodiment of the invention, a process for preparing a sheet-like or filmy pharmaceutical composition for trans-mucosal or transdermal administration which contains a step of casting a solution or suspension containing a per-$C_{2-18}$ acylated cyclodextrin as a solubilizing agent, adsorbent or clathrating agent, and a drug.

Further, it is possible to obtain a powdery or granular composition by dissolving peracylated β-CyD and a drug in an organic solvent, and distilling off the solvent by a rotary evaporator or the like. It is also possible to obtain a composition by heat melting peracylated β-CyD and a drug, cooling the melt, and if necessary, grinding the cooled matter.

Certain peracylated CyDs can be produced according to the process described in the above Chem. Pharm. Bull., 43 (1995), 130–136, and the acylated derivatives of CyDs used in the invention can, for example, be produced by dissolving β-CyD in anhydrous pyridine, adding an organic acid corresponding to the length of acyl group such as acetic anhydride or valeric anhydride at room temperature and under an anhydrous condition, and stirring with heating to around 80° C. After confirmation of the completion of the reaction with thin layer chromatography, the reaction solution is added to ice-water, the precipitate deposited and the oily matter were extracted with a solvent such as chloroform, the obtained extraction product is concentrated over anhydrous magnesium sulfate, and the concentrate is subjected to separation and purification by silica gel chromatography. Further, the purified product is dissolved in chloroform, the solution is sufficiently washed with an aqueous sodium carbonate solution and dried over anhydrous magnesium sulfate, the solvent is distilled off, and further, the residue is recrystallized from methanol to give purified acylated β-CyD.

In the composition according to the invention, the peracylated cyclodextrin and the drug exist in such a state that they are in a molecular state and can interact (e.g., the drug is clathrated in the CyD molecule), and the outside of the cyclodextrin molecule exhibits hydrophobicity and is good in contact with the skin or mucous membrane, and moreover, gives almost no irritation on them. Therefore, the drug is directly released from the composition to the cutis or mucosa. Namely, the movement of the drug molecule and the permeation thereof into the mucosa are possible without the aid of water or a solvent or the like.

Thus, according to the invention, there is provided a pharmaceutical composition for trans-mucosal or transdermal administration which is safe and excellent in the release behavior of the drug and skin permeability.

Hereinafter, examples are mentioned, aiming to describe the invention more specifically.

EXAMPLE (comparison) 1
Adhesive characteristic of pervaleryl-β-cyclodextrin

Pervaleryl-β-cyclodextrin (TV-β-CyD)-containing absolute ethanol solution (concentration: 150 mg/ml) was added dropwise onto a backing membrane (polyethylene terephthalate film) using a microsyringe, and allowed to stand at 25° C. for 24 hours to evaporate ethanol, whereby films of TV-β-CyD having adhesion were obtained.

The detaching force on the films of TV-β-CyD and on the films derived from various hydrophilic macromolecules (hydroxypropylcellulose (HPC), hydroxypropyl methylcellulose (HPMC) and polyhydroxyethyl methacrylate (PHEMA)) was measured using a probe tack tester (produced by Rigaku Kogyo Co.). The results are shown in FIG. 1. The films of hydrophilic macromolecules were prepared as described with respect to TV-β-CyD. The drawing shows that TV-β-CyD is the strongest in adhesion.

EXAMPLE (comparison) 2
Cutis irritativeness of per-TV-β-CyD

There was stuck 150 mg of TV-β-CyD, in the shape of a circle with a diameter of 20 cm, on the back of female hairless mice at the age of around 7 weeks (weight: 50–60 g), and 16 hours later, the cutis was extirpated. The extirpated cutis was fixed with 20% neutrally-buffered formalin solution and embedded in paraffin according to a usual manner, and tissue sections were prepared using a microtome. These sections were double stained with haematoxylin and Eosine, and observed by a light microscope. Untreated cutis was used as control. Moreover, a commercially available adhesive tape for patch test was applied on the same mice under the same condition, and, thereafter, the cutis tissue of the applied portion was extirpated for comparison. In the case of TV-β-CyD, there was observed peeling of corneum in the same degree as in the case of the commercially available adhesive tape. Other sites (control), however, showed no abnormality such as inflammatory cellular infiltration.

EXAMPLES (invention) 3 to 6
Adhesive characteristic of adhesive compositions and adhesive compositions containing an absorption enhancer Isosorbide dinitrate (ISDN) (3.4–6.7 mg) was dissolved in a TV-β-CyD-containing ethanol solution (concentration: 150 mg/ml), so as to give the following molar ratios, respectively, and each solution was added dropwise onto a backing membrane (polyethylene terephthalate film) using a microsyringe, and allowed to stand at 25° C. for 24 hours to evaporate ethanol, whereby an ISDN/TV-β-CyD composition having adhesion was obtained.

Isosorbide dinitrate (ISDN) (3.4–6.7 mg) was dissolved in a trivaleryl-β-cyclodextrin (TV-β-CyD)-containing ethanol solution (concentration: 150 mg/ml), respectively, and oleic acid (OA) was added (concentration: 4 w/v %). Each of the resultant solutions was added dropwise onto a backing membrane (polyethylene terephthalate film) using a microsyringe, and allowed to stand at 25° C. for 24 hours to evaporate ethanol, whereby an ISDN/TV-β-CyD/OA containing the absorption enhancer and having adhesion was obtained.

Figure 2:
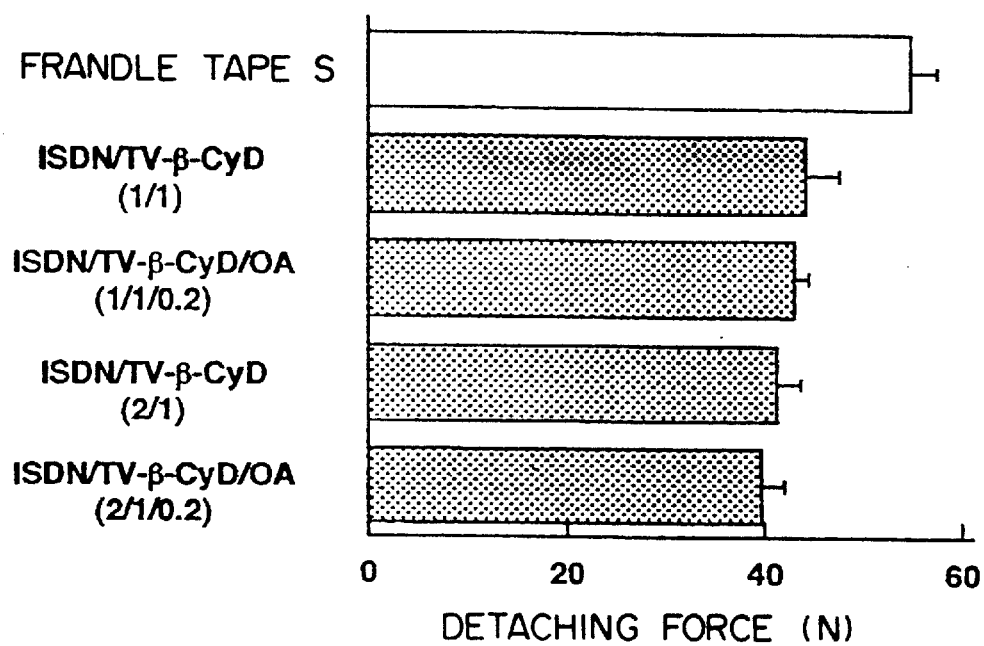
FIG. 2 is a graph which shows comparison on detaching force among the cohesive compositions, which contain the absorption enhancer and the isosorbide dinitrate preparation on the market, using a probe tack tester.

The adhesion of ISDN/TV-β-CyD (molar ratio 1/1: Example 3; 2/1: Example 5), ISDN/TV-β-CyD/OA (molar ratio 1/1/0.2: Example 4; 2/1/0.2: Example 6), and a commercially available isosorbide dinitrate preparation (Frandle Tape S, comparison) was measured using a probe tack tester (produced by Rigaku Kogyo Co.), and the results are shown in FIG. 2. As is seen apparently in the above, the present adhesive composition exhibits good adhesion even if it contains the absorption enhancer.

EXAMPLES (invention) 7 to 10
Drug release from adhesive compositions

Figure 3:
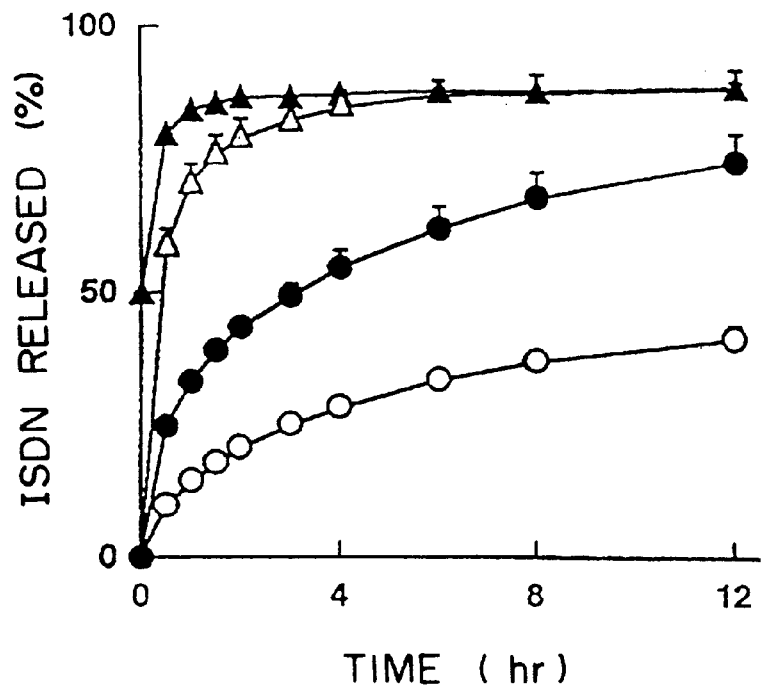
FIG. 3 is a graph which shows the drug release with time lapse from the adhesive compositions having different diameters and the isosorbide dinitrate preparation on the market, at 34° C., using the drug release measuring apparatus. The black triangular symbol shows Frandle Tape S, the white triangular symbol ISDN/TV-β-CyD (diameter: 3 cm), the black round symbol ISDN/TV-β-CyD (diameter: 2 cm), and the white round symbol ISDN/TV-β-CyD (diameter: 1 cm).
Figure 5:
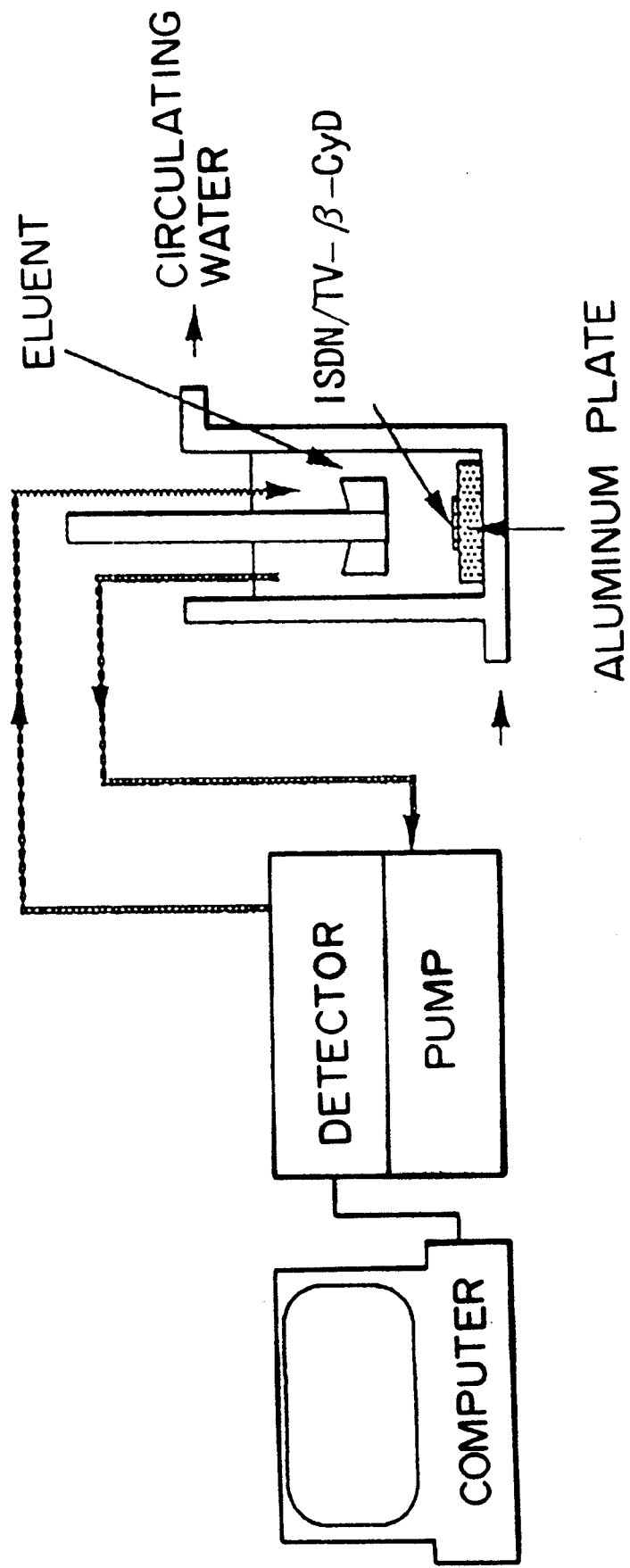
FIG. 5 is a schematic drawing of the apparatus for conducting the automatic dissolution test of the drug from the pharmaceutical composition.

ISDN/TV-β-CyDs having different diameters (diameter: 1 cm, 2 cm and 3 cm) were prepared in the same manner as in Examples 3 to 6. Drug release was measured according to the Second Method (Paddle Method) of Dissolution Test in the Japan Pharmacopeia XII using an automatic dissolution test apparatus (see FIG.5), in the following manner. ISDN/TV-β-CyD was fixed on an aluminum plate and put in a jacket beaker (inside diameter 5 cm, content volume 200 ml) through which circulating water of 34° C. was passed, and, then, 50 ml of deaerated eluent was introduced into said jacket beaker. The ISDN concentration was measured by a circulating UV detector (produced by SHIMADZU CORPORATION). For comparison, measurement was conducted on Frandle Tape S in the same manner. The results are shown in FIG. 3. The ISDN/TV-β-CyD having a diameter of 3 cm exhibited a release equivalent to Frandle Tape S, and, thus, a good drug release was shown.

Figure 4:
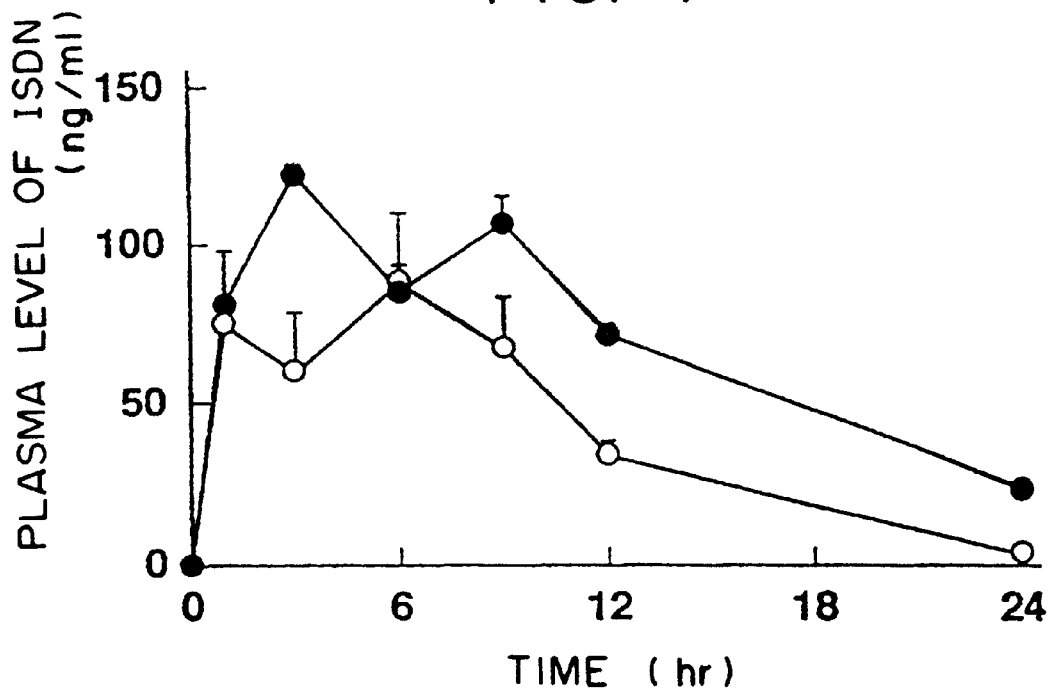
FIG. 4 is a graph which shows the isosorbide dinitrate concentration in the plasma with time lapse after the isosorbide nitrate/trivaleryl-β-cyclodextrin adhesive composition was administered onto the rat abdominal part. The black round symbol shows ISDN/TV-β-CyD/0A (molar ratio: 1/1/0.2) and the white round symbol shows ISDN/TV-β-CyD (molar ratio: 2/1).

EXAMPLES (invention) 11 to 12
Transdermal administration from cohesive composition ISDN/TV-β-CyD (molar ratio 2/1: Example 11) and ISDN/TV-β-CyD/OA (molar ratio 1/1/0.2: Example 12) were prepared in the same manner as in Examples 3 to 6. Wister male rats (weight: about 240 g) whose hair of the abdominal part had been removed under anesthetization were fixed on their backs, and the above ISDN/TV-β-CyD or ISDN/TV-β-CyD/OA was stuck on the unwounded part of each rat. Blood (0.6 ml) was taken with the lapse of time from the cervical vein using a syringe treated with heparin. To 0.2 ml of plasma from each of the obtained bloods, there was added 0.5 ml of 0.5M phosphate buffer, and extraction was conducted with 6 ml of chloroform. Then, the solvent was distilled off under reduced pressure. The residue was dissolved in mobile phase of methanol/water (1:4 v/v), and the ISDN concentration was measured by HPLC. The changes with time lapse of the ISDN concentration in the plasma after the administration to the abdominal parts of the rats are shown in FIG. 4. The values in the results are expressed as the mean±SE (n=3).

Each of the films maintained an ISDN concentration in the plasma of 40 ng/ml or more, which is an effective concentration, for 12 hours or more. Conditions of the above High-performance Liquid Chromatography (HPLC) were as follows:

Pump: 655 A-11 Type HPLC made by Hitachi Seisakusho K.K.

UV Detector: 655 A Type Wave Variable UV Monitor made by Hitachi Seisakusho K.K.

Integrator: D-2500 Type Chromato-Integrator made by Hitachi Seisakusho K.K.

Column: Shiseido Capsule PAK C8 SG120 Å(5 μm, 4.6 mm φ×300 mm)

Mobile Phase: methanol/water (1:4 v/v)

Flow Rate: 1.0 ml/min.

Measured Wave Length: 210 nm

EXAMPLE (invention) 13
Pharmaceutical composition applicable to oral mucous membrane containing triamcinolone White crystals (50 g) of perbutanoyl-β-cyclodextrin (TB-β-CyD) were dissolved in ethanol (200 ml), and, then, triamcinolone (12.6 g) was added. After stirring, drying with heating was conducted under reduced pressure at 60° C. for 3 hours. To the resultant powder (62 g), there were added lactose (120 g), corn starch (40 g), microcrystalline cellulose (Avicel® PH102: 18 g), hydroxypropylmethylcellulose [HPMC (TC-5. S: 6 g)] and magnesium stearate (0.04 g), and the mixture was uniformly mixed and tableted to give tablets administrable to oral mucosa.

A tablet contained the following components:

5 mg of triamcinolone 20 mg of TB-β-CyD 17 mg of lactose 7.5 mg of Avicel® PH102

2.5 mg of HPMC (TC-5. S), and trace amount of magnesium stearate

Total: 102 mg

The obtained tablets were tested for their characteristics (contents, fragileness and weight deviation) according to Preparation General Rules of The Japan Pharmacopeia Xll, and as a result they are found to be fit for all the test items. They were good in adhesion to the cheek, and adhesion was recognized to be durable. Further, there was no irritation to mucosa at the time of application.

We claim:

1. A process for preparing a sheet-like or filmy pharmaceutical composition for trans-mucosal or trans-dermal administration comprising the steps of:

(a) adding dropwise a solution or suspension of a per-$C_{2-18}$ acylated cyclodextrin and a drug in an organic solvent onto a backing membrane selected from aluminum foil, polyethylene terephthalate film or polystyrene film, and (b) volatilizing the solvent to form the pharmaceutical composition.

2. A process according to claim 1 wherein the acylated cyclodextrin is a per-$C_{4-6}$ acylated β-cyclodextrin.

* * * * *